US012228628B2

(12) United States Patent
Grodzki (10) Patent No.: US 12,228,628 B2
(45) Date of Patent: Feb. 18, 2025

(54) METHOD FOR IMPROVED POSITIONING OF SLICES IN WHICH MEASUREMENT DATA IS TO BE RECORDED USING A MAGNETIC RESONANCE SYSTEM

(71) Applicant: Siemens Healthcare GmbH, Erlangen (DE)

(72) Inventor: David Grodzki, Erlangen (DE)

(73) Assignee: Siemens Healthineers AG, Erlangen (DE)

( * ) Notice: Subject to any disclaimer, the term of this patent is extended or adjusted under 35 U.S.C. 154(b) by 117 days.

(21) Appl. No.: 18/091,624

(22) Filed: Dec. 30, 2022

(65) Prior Publication Data
US 2023/0213602 A1 Jul. 6, 2023

(30) Foreign Application Priority Data
Dec. 30, 2021 (DE) .......................... 102021215124.8

(51) Int. Cl.
*G01V 3/00* (2006.01)
*A61B 5/055* (2006.01)
(Continued)

(52) U.S. Cl.
CPC ............ *G01R 33/543* (2013.01); *A61B 5/055* (2013.01); *G01R 33/4835* (2013.01)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS 10,101,421 B2 * 10/2018 Grodzki ............... G01R 33/543
2004/0160221 A1 * 8/2004 Kiefer .............. G01R 33/56518
324/309
(Continued)

FOREIGN PATENT DOCUMENTS

DE 10250913 A1 5/2004
EP 4102244 A1 12/2022

OTHER PUBLICATIONS

Doran, Simon J. et al. "A Complete Distortion Correction for MR Images: I. Gradient Warp Correction" Physics in Medicine and Biology, vol. 50, pp. 1343-1361, 2005.

*Primary Examiner* — Walter L Lindsay, Jr.
*Assistant Examiner* — Frederick Wenderoth
(74) *Attorney, Agent, or Firm* — Banner & Witcoff Ltd.

(57) ABSTRACT

In a method to improved positioning of slices in which measurement data is to be recorded, a planning image of an examination object is provided that has been distortion-corrected using non-linearity data describing a non-linearity of a gradient unit of the magnetic resonance system, a desired field of view and desired slices in the at least one planning image are selected, a measurement protocol to record the measurement data is loaded, switchable gradients and/or emittable RF pulses are adapted, as a function of the non-linearity data that has been loaded and the desired slices, such that the desired slices are excited despite the non-linearities of the gradient unit, and the loaded measurement protocol is performed in the selected field of view, using the adapted gradients to be switched and/or adapted RF pulses. The measurement protocol may include switchable gradients and the emittable RF pulses.

17 Claims, 3 Drawing Sheets

(51) Int. Cl.
 *G01R 33/54* (2006.01)
 *G01R 33/483* (2006.01)
(58) Field of Classification Search
 USPC .......................................................... 324/309
 See application file for complete search history.

(56) References Cited

U.S. PATENT DOCUMENTS

| | | | |
|---|---|---|---|
| 2012/0262171 A1* | 10/2012 | Weber | G01R 33/4836 |
| | | | 324/309 |
| 2014/0021950 A1* | 1/2014 | Grodzki | G01R 33/42 |
| | | | 324/307 |
| 2014/0232369 A1 | 8/2014 | Hogan | |
| 2015/0235369 A1* | 8/2015 | Ishida | A61B 5/0033 |
| | | | 382/131 |
| 2016/0124065 A1* | 5/2016 | Pfeffer | G01R 33/56563 |
| | | | 324/309 |
| 2019/0113588 A1* | 4/2019 | Tamura | G01R 33/543 |
| 2022/0397623 A1 | 12/2022 | Paul et al. | |

\* cited by examiner

FIG 1

METHOD FOR IMPROVED POSITIONING OF SLICES IN WHICH MEASUREMENT DATA IS TO BE RECORDED USING A MAGNETIC RESONANCE SYSTEM

CROSS REFERENCE TO RELATED APPLICATIONS

This patent application claims priority to German Patent Application No. 10 2021 215 124.8, filed Dec. 30, 2021, which is incorporated herein by reference in its entirety.

BACKGROUND

Field

The disclosure relates to a method for improved positioning of slices in which measurement data is to be recorded by means of a magnetic resonance system, and to a magnetic resonance system, a computer program product and an electronically readable data medium.

Related Art

Magnetic resonance technology (the abbreviation MR signifies magnetic resonance in the following) is a known technology by means of which images of the interior of an examination object can be produced. To this end, expressed simply, the examination object is positioned in a magnetic resonance device in a comparatively strong static homogeneous basic magnetic field, also known as the $B_0$ field, having field strengths of 0.2 tesla to 7 tesla and more, such that the nuclear spins thereof are oriented along the basic magnetic field. In order to trigger nuclear spin resonances that can be measured as signals, high-frequency excitation pulses (RF pulses) are emitted into the examination object, the triggered nuclear spin resonances are measured as so-called k-space data, and MR images are reconstructed or spectroscopy data is determined on the basis thereof. In order to achieve spatial encoding of the measurement data, rapidly switched gradient fields (also referred to simply as gradients) are superimposed on the basic magnetic field. A model which describes a temporal sequence of RF pulses that are to be emitted and gradients that are to be switched is called a pulse sequence (model) or simply a sequence. Once it has been recorded, the measurement data is digitized and stored as complex numerical values in a k-space matrix. A corresponding MR image can be reconstructed from the k-space matrix to which the values have been assigned, e.g. by means of a multidimensional Fourier transformation.

The gradient fields that are used for the spatial encoding are ideally so generated as to produce a linearity that is as precise as possible, while the basic magnetic field should be as homogeneous as possible.

However, imperfections in the gradient fields can occur, in particular due to the respective nature of the gradient coils of a gradient unit, and result in a deviation from the ideal linearity. Such deviations and associated non-linearities of the gradient fields of the gradient unit can also be selectively tolerated when developing the gradient coils of a gradient unit, e.g. in order to configure the gradient coils of the gradient unit to be particularly thin, quiet and/or inexpensive. As a result of these non-linearities, stronger or weaker rises of the gradient fields may be required than in the case of continuous linearity at a given location in the measuring volume of the magnetic resonance system comprising the gradient unit.

Such non-linearities of a gradient unit can result in distortions during the spatial encoding, e.g. stretching and/or compression, which occur mainly in outer regions of MR images that are reconstructed from measurement data recorded thus, and which depend on the gradient unit used (in particular the type of gradient coils) or the distortion characteristics thereof and on the measurement protocol (in particular the pulse sequence) that is used for the recording of the measurement data.

So-called distortion corrections can be used to overcome the non-linearities with the aid of previously stored distortion information, in particular a distortion map, by effecting image-based displacements of the corresponding image points. For example, the prior art discloses the use of a phantom whose geometry is known in respect of at least some marker points, to carry out a calibration measurement in order to specify a distortion map in respect of the non-linearity of the gradient fields of the gradient unit for a specific magnetic resonance system. Such a distortion map then describes corresponding distortion coefficients which define how a given image point must be displaced. Such distortion correction can be applied in both two-dimensional (2D) MR image data records and three-dimensional (3D) MR image data records.

In most cases, the planning (placement and position of the region of interest of an examination object, also called "field of view" or FOV) of MR measurements that are to be performed is already based in most cases on distortion-corrected MR (reference) images, e.g. so-called localizers. Planning that is based on distortion-corrected MR images has many advantages, e.g. distortions caused by the non-linearities of the gradient unit are not visible in the distortion-corrected MR image, and therefore e.g. distances can be determined without distortion in the distortion-corrected MR image. Furthermore, if non-distortion-corrected MR images were used for the purpose of planning, a new MR reference image would have to be recorded following any (often necessary) movement of the couch of the magnetic resonance system between planning and performance of the measurement, in order that valid distortions could be displayed for the new position of the couch.

It is problematic here that, depending on the direction of the image point displacement which takes place in the context of the distortion correction, the field of view that is actually set, generally defined as a rectangle or square, may be reduced. This is because the recording of the measurement data is performed during the measurement using the non-linear gradient fields of the gradient unit, and can therefore cover a different region of the examination object than could be expected from planning that is based on the distortion-corrected MR images. It can therefore occur that, owing to the distortion, specific regions (in particular at the edge) of MR image data records are not captured during the recording of the measurement data and are consequently not depicted, such that no data is available for these non-depicted regions.

This difficulty is amplified in the case of measurements in edge regions of the homogeneity volume of the basic magnetic field and also in the case of more modern magnetic resonance systems which can be configured more openly and freely.

Figure 1:
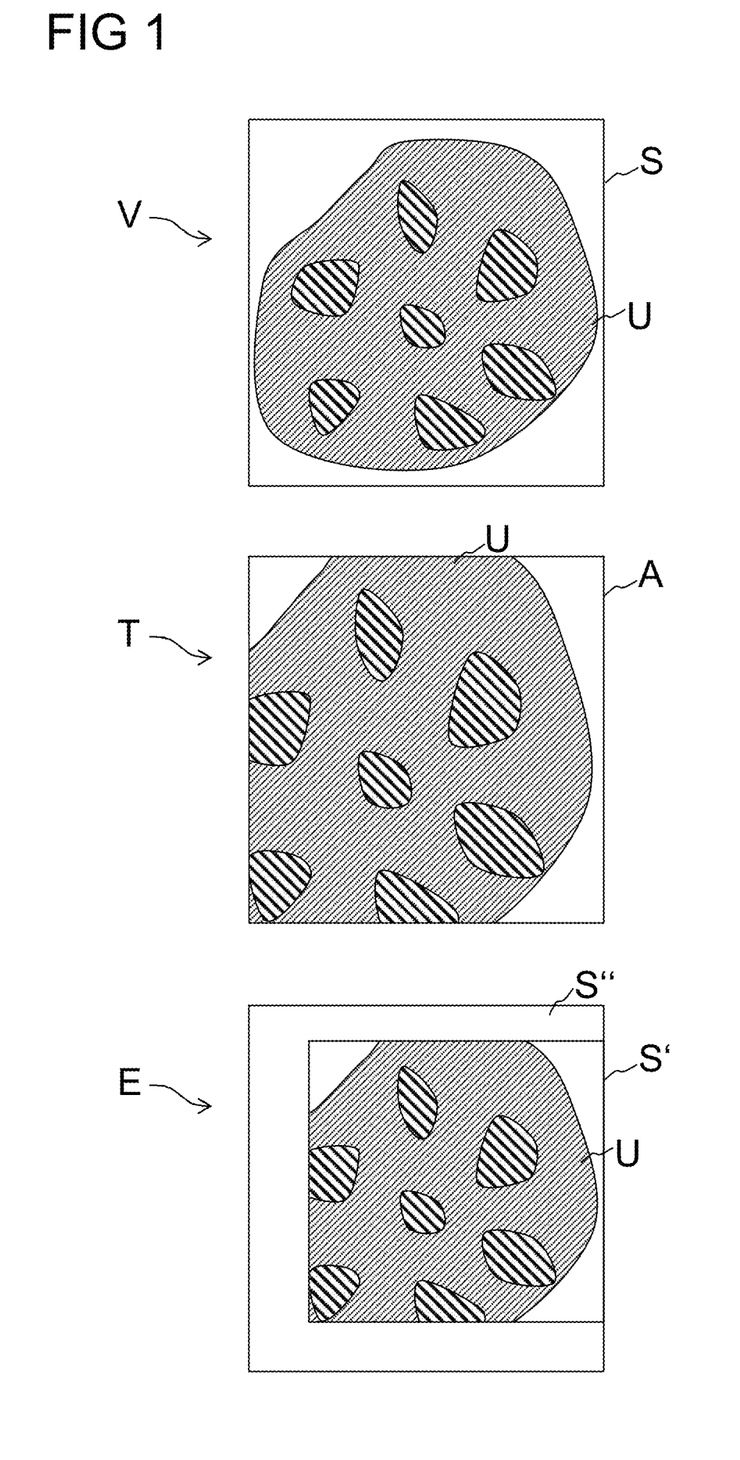
FIG. 1 includes example MR images according to the disclosure.

This problem is illustrated in FIG. 1, which schematically shows a region of interest S that is selected within a distortion-corrected MR image V and, in said region of interest S, a region to be depicted of an examination object U. The region of interest S that is selected within the distortion-corrected MR image V is then shown in a region A that is selected within an actual non-distortion-corrected image T, measurement data being recorded from region A on the basis of this selection. The result of the recording of measurement data thus performed is shown in the again distortion-corrected MR image E, in which, as shown in the marked region S', only measurement data for that region of the examination object U which corresponds to the region A is depicted, and no measurement data is available for a region S". The resulting MR image E appears to be "cut off" and such interference is therefore also referred to as "cropping".

In order to prevent such cropping, as disclosed in e.g. EP21178419, regions that can be "cut off" are already displayed to a user in the distortion-corrected MR image that is used for the planning, so that a correspondingly enlarged region of interest can be selected for the recording of the measurement data, in order to avoid cropping effects. Such a method of enlarging the FOV can nonetheless only prevent the described problem in a phase encoding direction and a readout direction ("in-plane") of the MR images that are used for the planning.

However, it is actually effects in a slice direction that represent a particular difficulty and are hard for a user to understand. If slices are planned on distortion-corrected MR images, their spatial position in the actual recording of the measurement data can lie at a position that deviates from the planned position. Slices thus planned are distorted, such that their shape no longer lies in a plane but is instead deformed in the manner of potato chips, for example.

As a result of the distortion correction, and particularly in the case of off-center measurements (i.e. recordings of measurement data outside the center of the homogeneity region of the basic magnetic field of the magnetic resonance system concerned), it can therefore easily occur that of e.g. ten planned and measured slices, not all ten but e.g. only four or even only two are provided to the user after recording the measurement data and performing the distortion correction, because the other slices lie in regions that are situated outside the required coverage. This is not obvious beforehand or during the planning and cannot be compensated simply by larger FOVs as in the case of in-plane distortions.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the disclosure is to allow improved positioning of slices in which measurement data is to be recorded by a magnetic resonance system.

The object is achieved by a method for improved positioning of slices in which measurement data is recorded by means of a magnetic resonance system, a magnetic resonance system, a computer program product, and an electronically readable data medium.

A method according to an exemplary embodiment of the disclosure for improved positioning of slices in which measurement data is to be recorded by means of a magnetic resonance system, may include the steps:

loading non-linearity data which describes a non-linearity of a gradient unit of the magnetic resonance system, displaying, e.g. on a user interface of the magnetic resonance system, at least one planning image of an examination object which is situated in a measuring volume of the magnetic resonance system, said planning image being distortion-corrected using the non-linearity data that was loaded, selecting a desired field of view and desired slices in the at least one planning image, loading a measurement protocol to be used for the recording of the measurement data, said measurement protocol comprising gradients that are to be switched and RF pulses that are to be emitted, adapting gradients that are to be switched and/or RF pulses that are to be emitted according to said measurement protocol, as a function of the non-linearity data that has been loaded and the desired slices, such that the desired slices are excited despite the non-linearities of the gradient unit, performing the loaded measurement protocol in the selected field of view, using the adapted gradients to be switched and/or adapted RF pulses, by means of a pulse sequence unit of the magnetic resonance system.

As a result of inventively adapting, as a function of the non-linearity data that has been loaded and the desired slices, gradients that are to be switched and/or RF pulses that are to be emitted according to the measurement protocol, it is possible to achieve an automatic correction of the positions of the slices that are actually measured, such that a measurement takes place in desired slices required by a user despite non-linearities of the gradient unit concerned.

Non-linearity data describing a non-linearity of a gradient unit of the magnetic resonance system can be loaded in the form of a distortion map.

The distortion map is considered to be specific to a magnetic resonance entity, at least with regard to the imperfections of the gradient fields, meaning that a distortion map which has been determined on the basis of a calibration is known and held in a memory device of the controller.

Therefore, knowledge that is used in the context of distortion correction also includes which spatial displacements actually occur. The concept underlying the disclosure is then to use this knowledge of the distortion map in advance of a magnetic resonance recording, in order to allow improved adjustment of the position and placement of desired slices in which a recording of measurement data takes place.

A magnetic resonance system according to the disclosure comprises a magnet unit, a gradient unit, a high-frequency unit and a controller with a compensation gradient specification unit, which is designed to perform a method according to the disclosure.

A computer program product according to the disclosure implements a method according to the disclosure on a controller when executed on said controller. The computer program product may be embodied on a non-transitory computer-readable medium.

In this context, the computer program product can be loaded directly into a memory of a controller and has program code means for executing a method according to the disclosure when the computer program product is executed in the computing unit of the computing system.

An electronically readable data medium according to the disclosure has stored thereon electronically readable control information which comprises at least a computer program according to the disclosure and is configured in such a way as to perform a method according to the disclosure when the data medium is used in a controller of a magnetic resonance system.

The advantages and explanations specified in relation to the method apply analogously to the magnetic resonance system, the computer program product and the electronically readable data medium likewise.

Figure 2:
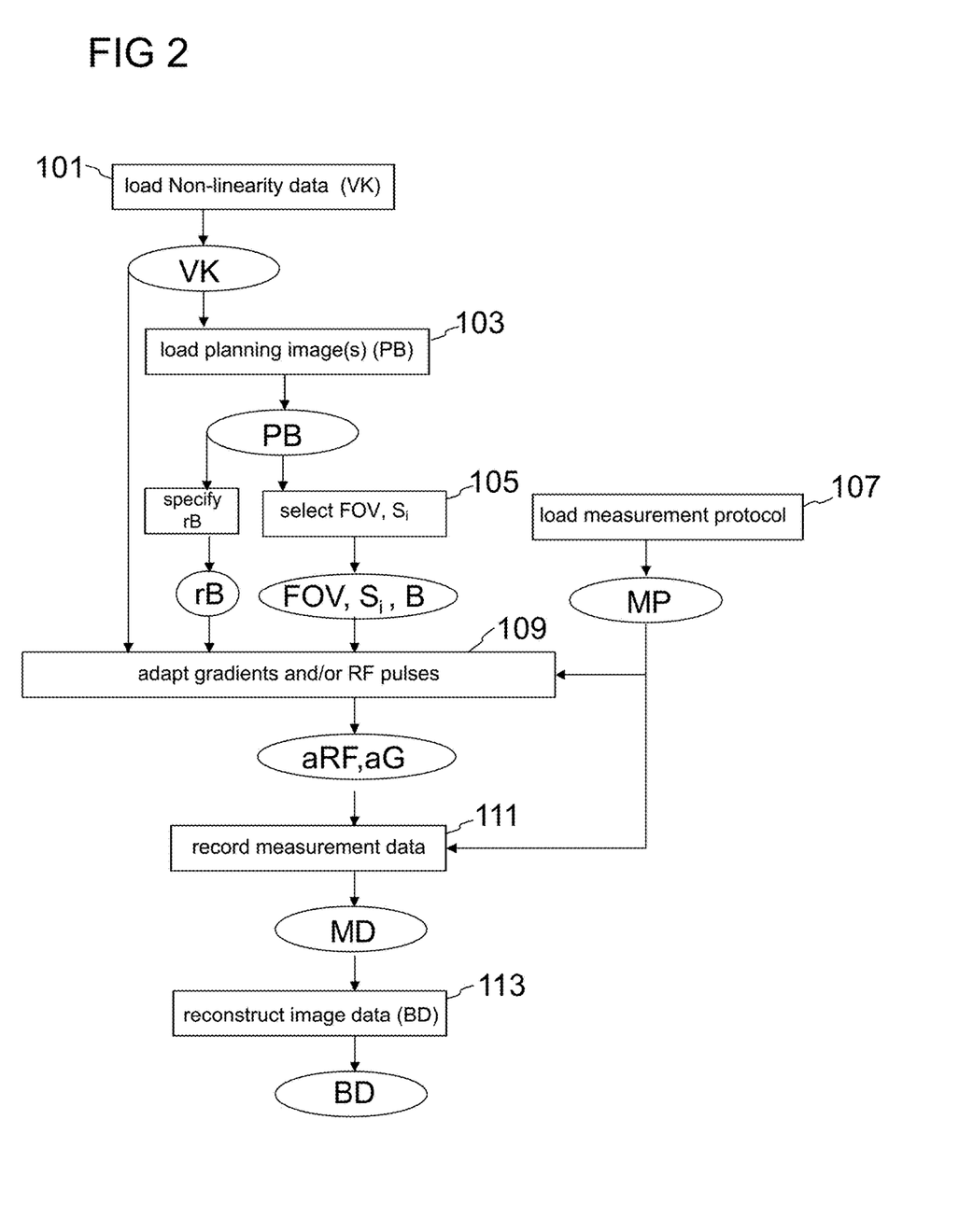
FIG. 2 is a flowchart of a method according to an exemplary embodiment of the disclosure.

FIG. 2 is a schematic sequence diagram of a method according to the disclosure for improved positioning of slices in which measurement data MD is recorded by means of a magnetic resonance system.

Non-linearity data VK is loaded (block 101), said non-linearity data VK describing a non-linearity of a gradient unit 5 of the magnetic resonance system 1. As cited above, the non-linearity data VK can be loaded in the form of e.g. a distortion map which is known per se. Such distortion maps VK are usually specified at least during the installation of a magnetic resonance system and are available e.g. in a memory thereof.

At least one planning image PB of an examination object U situated in a measuring volume of the magnetic resonance system 1 is loaded (block 103), said planning image PB being distortion-corrected using the non-linearity data that was loaded. Such planning images PB are normally recorded before the start of a MR measurement, in order to ensure that measurement data is recorded in a desired region of interest of the examination object concerned. The display of the at least one planning image PB can take place at e.g. a user interface 27 of the magnetic resonance system 1.

A desired field of view FOV and desired slices $S_i$ are selected (block 105) in the at least one planning image PB, e.g. at a user interface 27 of the magnetic resonance system 1. This is part of a standard procedure that would normally be carried out by a user.

A measurement protocol MP that is to be used for recording the measurement data is loaded (block 107), said measurement protocol MP comprising gradients that are to be switched and RF pulses that are to be emitted. The measurement protocol specifies in particular a pulse sequence to be used for the recording of the measurement data, and therefore specifies how the measurement data is to be recorded and which contrasts are achieved during this activity.

Gradients that are to be switched and/or RF pulses that are to be emitted according to a measurement protocol MP are adapted (block 109) as a function of the loaded non-linearity data VK and the desired slices $S_i$ in such a way that the desired slices $S_i$ will be excited or if applicable manipulated by the emitted RF pulses despite the non-linearities of the gradient unit 5, whereby adapted gradients aG to be switched and/or adapted RF pulses aRF to be emitted are obtained.

Figure 3:
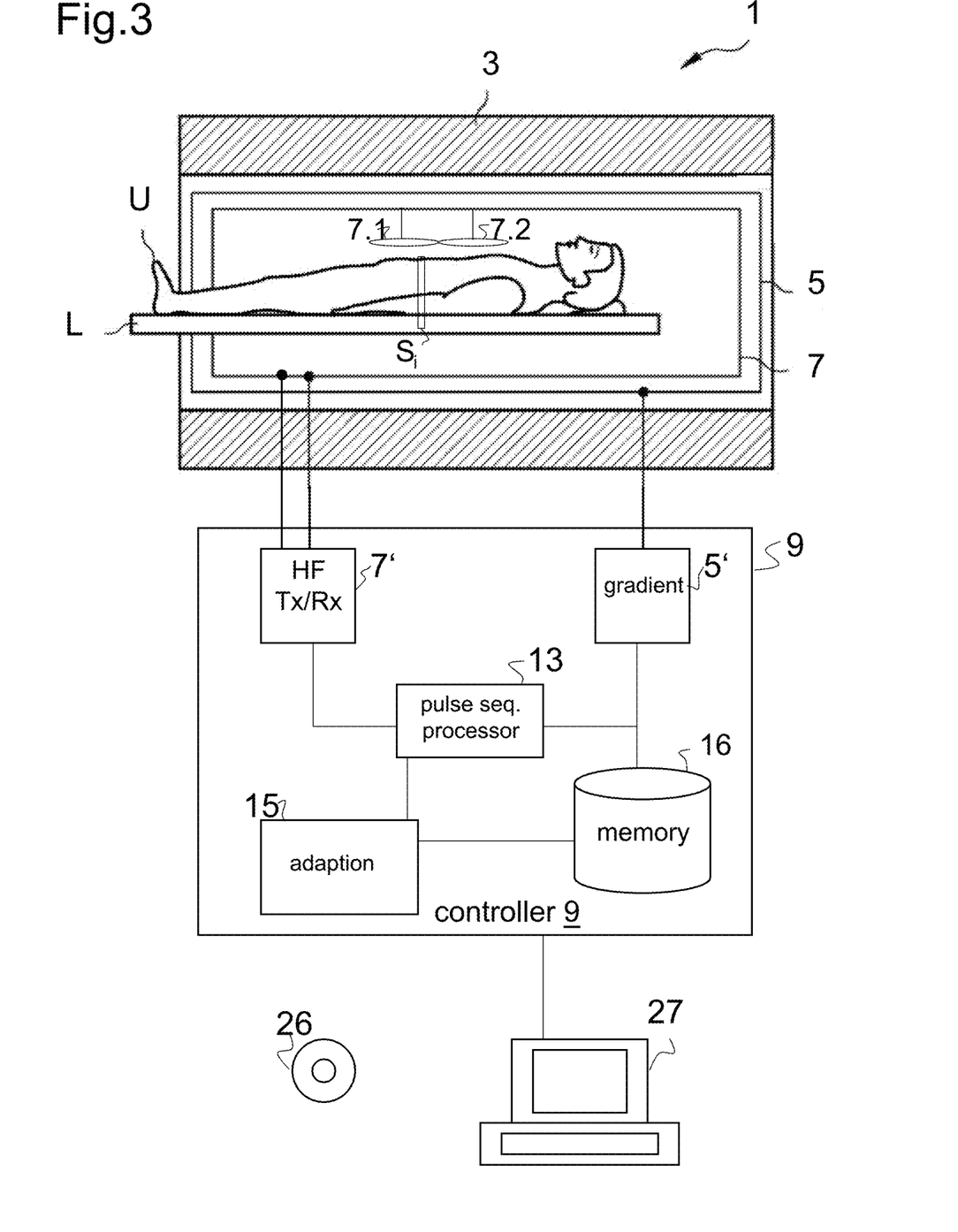
FIG. 3 shows a magnetic resonance system according to an exemplary embodiment of the disclosure.

Such an adaptation of gradients that are to be switched and/or RF pulses that are to be emitted according to a measurement protocol MP can be performed e.g. in an adaptation unit 15 which is connected between user interface 27 and a pulse sequence unit 13 of the magnetic resonance system 1. This has the advantage that existing calculations and implementations in the pulse sequence unit 13 and in the user interface 27, which are also valid without the inventive method, need not be adapted. It is therefore possible e.g. to avoid changes to the source code of the individual pulse sequences, and instead to implement the functionality of the inventive adaptation centrally.

Selecting a desired field of view FOV and desired slices $S_i$ in the at least one planning image PB can include identifying at least one partial region B along the desired slices $S_i$, the gradients that are to be switched and/or RF pulses that are to be emitted according to a measurement protocol MP then being optimally adapted in said partial region B.

Such a selection of partial regions B can contribute to an optimized positioning of the slices, since slices as two-dimensional objects can be subject to non-linearities along not just one spatial direction but in both spatial directions, and the slices are often deformed in the manner of potato chips. If the adaptation of the gradients that are to be switched and/or the RF pulses that are to be emitted is optimized for the selected partial region B of the desired slices $S_i$, adapted gradients aG and/or adapted RF pulses aRF for this selected slice region B can be specified more easily and more quickly, while for the further slices, which are not situated in the partial region B and for which less value is placed on an exact positioning, an average value of the distortion or a central slice region can be sufficient as a calculation basis for adapted gradients aG and/or adapted RF pulses aRF.

The adaptation of the gradients that are to be switched and/or RF pulses that are to be emitted according to a measurement protocol MP can also be optimized automatically in regions rB which are specified as relevant on the basis of landmarks specified in the at least one planning image. The advantages cited in respect of the partial regions B selected by a user apply analogously to such relevant regions rB. Moreover, no action by a user is required because the specification of the relevant regions rB takes place automatically. A specification of the landmarks can take place using a conventional segmentation method, for example. The specification of relevant regions rB can take place on the basis of the landmarks and relevant regions to be depicted, e.g. (partial) organs, which are e.g. known from the type of the measurement to be performed.

Adapted gradients aG to be switched according to a measurement protocol can be slice selection gradients in particular. Slice selection gradients contribute significantly to the encoding of the slice position. Adapted RF pulses aRF to be emitted can be slice excitation pulses in particular, these being responsible for the excitation of the spins from which echo signals are to be recorded as measurement data.

As a result of the adaptation, gradients that are to be switched according to a measurement protocol can be adapted using the non-linearity data VK, in particular such that the gradients that are nominally to be switched according to a measurement protocol MP are actually achieved despite the non-linearity of the gradient unit.

It is however also conceivable to not completely adapt the gradients that are to be switched to the extent that their nominal strength is actually achieved, and instead to perform an adaptation that goes only some way towards the nominal strength. Consequently remaining distortions can be compensated by an additional adaptation of the RF pulses that are to be emitted, e.g. as described later in the text.

It can be advantageous in principle to limit adaptations of the gradients that are to be switched to a degree that avoids losing, due to the adaptation, corrections which might already be integrated in the measurement protocol in respect of Maxwell terms and/or eddy current effects resulting from the gradients that are to be switched. In order to preserve such corrections completely, it is also possible entirely to forgo any adaptation of the gradients that are to be switched according to a measurement protocol, and to achieve the optimization of the positioning of the slices solely by adapting the RF pulses that are to be emitted according to a measurement protocol.

Adapting an RF pulse that is to be emitted can include specifying a position and thickness of a desired slice $S_i$ on the basis of the RF pulse that is to be emitted according to a measurement protocol and the gradients that are to be switched according to a measurement protocol in a slice selection direction with the RF pulse that is to be emitted. Such a specification of a desired slice $S_i$, from the RF pulse that is to be emitted and the associated gradients that are to be switched according to a measurement protocol MP, delivers the position and thickness which are desired by a measurement protocol in respect of the desired slice, and which are to be achieved despite the non-linearity of the gradient unit 5.

Adapting an RF pulse that is to be emitted can include, for the specified position of the desired slice $S_i$, with reference to the non-linearity data VK, specifying a gradient that is actually achieved using the gradient which, according to a measurement protocol MP, is to be switched concurrently with the RF pulse that is to be adapted. It is thus possible with reference to the non-linearity data to ascertain how a gradient that is to be switched according to a measurement protocol deviates from a gradient which, for the purpose of positioning a slice, is to be switched according to the specified position of the desired slice $S_i$.

Adapting an RF pulse that is to be emitted can include, with reference to the non-linearity data VK, specifying a bandwidth of the RF pulse, which bandwidth has been adapted for the specified position of the desired slice $S_i$. It is thus possible with reference to the non-linearity data to ascertain how a bandwidth of an RF pulse that is to be emitted according to a measurement protocol and adapted deviates from a bandwidth that is required, for the purpose of positioning a slice, according to the specified position of the desired slice $S_i$.

Adapting an RF pulse that is to be emitted can include, with reference to the non-linearity data VK, specifying a frequency of the RF pulse, which frequency has been adapted for the specified position of the desired slice $S_i$. It is thus possible with reference to the non-linearity data to ascertain how a frequency of an RF pulse that is to be emitted according to a measurement protocol and adapted deviates from a frequency that is required, for the purpose of positioning a slice, according to the specified position of the desired slice $S_i$.

Adapting an RF pulse that is to be emitted can therefore include adapting the frequency and/or the bandwidth of the RF pulse as a function of the specified gradient that is actually achieved and the specified position of the desired slice. It is thus possible with reference to the adapted RF pulses and if applicable adapted gradients to excite or manipulate desired slices at the planned positions, so that measurement data can be recorded from the planned desired slices.

The loaded measurement protocol MP is performed by a pulse sequence unit 13 of the magnetic resonance system 1 for the selected field of view FOV, using the adapted gradients aG to be switched and/or the adapted RF pulses aRF, such that measurement data MD is recorded (block 111) in the desired slices $S_i$.

Image data BD can be reconstructed and optionally displayed and/or stored (block 113) from the recorded measurement data MD.

FIG. 3 schematically illustrates a magnetic resonance system 1 according to the disclosure. This comprises a magnet unit 3 for generating the basic magnetic field, a gradient unit (gradient generator) 5 configured to generate the gradient fields, a high-frequency (HF) unit (HF transceiver) 7 configured to emit and receive high-frequency signals, and a controller 9 which is configured to perform a method according to the disclosure. In an exemplary embodiment, the controller 9 includes processing circuitry that is configured to perform one or more operations of the controller 9. The magnet unit 3, the gradient unit (gradient generator) 5, and the high-frequency (HF) unit (HF transceiver) 7 may be components of a MR scanner. The MR scanner may include one or more other components, such as coils 7.1, 7.2, patient couch L, and/or one or more other components as would be understood by one of ordinary skill in the arts.

FIG. 6 only provides an approximate schematic illustration of these subunits of the magnetic resonance system 1. In particular, the high-frequency unit 7 can consist of a plurality of subunits, e.g. a plurality of coils such as the coils 7.1 and 7.2 that are schematically shown, or more coils which can be configured to either only transmit high-frequency signals or only receive the triggered high-frequency signals, or both.

In order to examine an examination object U, e.g. a patient or even a phantom, the examination object U can be introduced into the measuring volume of the magnetic resonance system 1 on a couch L. The slice or the slab $S_i$ represents an exemplary target volume of the examination object, from which echo signals are to be recorded and captured as measurement data.

The controller 9 is used to control the magnetic resonance system 1 and in particular can control the gradient unit 5 by means of a gradient controller 5' and the high-frequency unit 7 by means of a high-frequency transmit/receive controller 7'. The high-frequency unit 7 here can comprise a plurality of channels on which signals can be transmitted or received.

The high-frequency unit 7 together with its high-frequency transmit/receive controller 7' is responsible for the generation and emission (transmission) of a high-frequency alternating field for the purpose of manipulating the spin in a region that is to be manipulated (e.g. in the slices S to be measured) of the examination object U. In this case, the center frequency of the high-frequency alternating field, also referred to as the $B_1$ field, is normally if possible adjusted to be close to the resonant frequency of the spins that are to be manipulated. Deviations of the center frequency from the resonant frequency are referred to as off-resonance. For the purpose of generating the $B_1$ field, controlled currents are applied to the HF coils in the high-frequency unit 7 by means of the high-frequency transmit/receive controller 7'.

A pulse sequence unit (pulse sequence processor) 13 contained in the controller 9 is designed to execute all the computing operations that are required to calculate the RF pulses to be emitted and gradients to be switched for the measurements and specifications that are necessary. Intermediate results and results that are required for or obtained during this activity can be stored in a memory unit 16 of the controller 9. The illustrated units here do not necessarily signify physically separate units, but merely represent a subdivision into logical units which can nonetheless also be realized e.g. in fewer units or even in a single physical unit.

The controller 9 further comprises an adaptation unit 15 by means of which RF pulses and/or gradients that are to be switched can be adapted according to the disclosure and implemented by the pulse sequence unit 13. The controller 9 as a whole is designed to perform a method according to the disclosure. In an exemplary embodiment, one or more components (e.g. 5', 7', 13, 15, 16) of the controller 9 includes processing circuitry that is configured to perform one or more respective operations of the component(s).

A user interface 27 of the magnetic resonance system 1 for the input and output of data and information can be used, e.g. by a user, to send control commands to the magnetic resonance system and/or to display results of the controller 9 such as e.g. image data.

A method described herein can also be provided in the form of a computer program product which comprises a program and implements the described method on a controller 9 when it is executed on the controller 9. Likewise, an electronically readable data medium 26 can be provided, on which is stored electronically readable control information comprising at least a computer program product such as that described above and being configured to perform the described method when the data medium 26 is used in a controller 9 of a magnetic resonance system 1.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for improved positioning of slices in which measurement data is to be recorded by means of a magnetic resonance system, comprising the steps:
   loading, by a controller of the magnetic resonance system, non-linearity data describing a non-linearity of a gradient unit of the magnetic resonance system, the controller including an adaptation unit and a pulse sequence unit;
   providing, using a user interface of the magnetic resonance system, at least one planning image of an examination object situated in a measuring volume of the magnetic resonance system, the planning image being distortion-corrected based on the non-linearity data;
   selecting, using the user interface, a desired field of view (FOV) and desired slices in the at least one planning image;
   loading, by the pulse sequence unit, a measurement protocol configured for recording of the measurement data, the measurement protocol including switchable gradients and emittable radio-frequency (RF) pulses;
   adapting, by the adaptation unit, the switchable gradients and/or the emittable RF pulses based on the measurement protocol, as a function of the non-linearity data and the desired slices, such that the desired slices are excited despite the non-linearities of the gradient unit, wherein the adaptation unit is connected between the user interface and the pulse sequence unit; and
   controlling, by the controller, the pulse sequence unit to perform the loaded measurement protocol in the selected field of view, using the adapted switchable gradients and/or adapted RF pulses, to record the measurement data.

2. A magnetic resonance (MR) system comprising:
   a user interface;
   a MR scanner including a gradient unit; and
   a controller comprising a pulse sequence unit and an adaptation unit, wherein the adaptation unit is connected between the user interface and the pulse sequence unit, the controller being configured to:
     load non-linearity data describing a non-linearity of the gradient unit;
     provide, using the user interface, at least one planning image of an examination object situated in a measuring volume of the MR scanner, the planning image being distortion-corrected based on the non-linearity data;
     select, using the user interface, a desired field of view (FOV) and desired slices in the at least one planning image;
     control the pulse sequence unit to load a measurement protocol configured for recording of measurement data, the measurement protocol including switchable gradients and emittable radio-frequency (RF) pulses;
     control the adaptation unit to adapt the switchable gradients and/or the emittable RF pulses based on the measurement protocol, as a function of the non-linearity data and the desired slices, such that the desired slices are excited despite the non-linearities of the gradient unit; and
     control the pulse sequence unit to perform the loaded measurement protocol in the selected field of view, using the adapted switchable gradients and/or adapted RF pulses, to record the measurement data.

3. The method as claimed in claim 1, wherein the non-linearity data is loaded as a distortion map.

4. The method as claimed in claim 1, wherein the switchable gradients are adapted using the non-linearity data such that the switchable gradients are realized.

5. The method as claimed in claim 1, wherein the RF pulses are adapted, the adapting of the RF pulse including specifying a position and a thickness of a desired slice based on: the RF pulse to be emitted according to the measurement protocol, and the switchable gradient in a slice direction with the RF pulse.

6. The method as claimed in claim 1, wherein selecting the desired field of view and the desired slices in the at least one planning image includes identifying at least one relevant partial region of the field of view along the desired slices, the adapted switchable gradients and/or emittable RF pulses being optimized in the identified at least one relevant partial region.

7. The method as claimed in claim 1, wherein the adaptation of the switchable gradients and/or emittable RF pulses are optimized automatically in regions having been specified as relevant based on landmarks specified in the at least one planning image.

8. The method as claimed in claim 1, wherein adapted gradients that are to be switched according to a measurement protocol are slice selection gradients and adapted RF pulses that are to be emitted are slice excitation pulses.

9. A computer program product, embodied on a non-transitory computer-readable storage medium, having a computer program and that is directly loadable into a memory of a controller of the magnetic resonance system, when executed by the controller, causes the magnetic resonance system to perform the method as claimed in claim 1.

10. A non-transitory computer-readable storage medium with an executable program stored thereon, that when executed, instructs a processor to perform the method of claim 1.

11. The MR system as claimed in claim 2, wherein the controller is further configured to provide the measurement data in electronic form as a data file.

12. The MR system as claimed in claim 2, wherein the controller is further configured to control the user interface to display the recorded measurement data.

13. The MR system as claimed in claim 2, wherein the controller is further configured to store the recorded measurement data in a memory of the controller and/or an external memory.

14. The method as claimed in claim 1, further comprising providing, by the controller, the recorded measurement data in electronic form as a data file.

15. The method as claimed in claim 5, wherein adapting the RF pulse, for a specified position of a slice of the desired slices, based on the non-linearity data, specifying a gradient achieved using the switchable gradient with the adapted RF pulse.

16. The method as claimed in claim 5, wherein the adapting of the RF pulse comprises, with reference to the non-linearity data, specifying a bandwidth of the RF pulse, the bandwidth having been adapted for a specified position of the desired slice.

17. The method as claimed in claim 5, wherein the adapting of the RF pulse comprises adapting a frequency and/or a bandwidth of the RF pulse based on the specified gradient that has been achieved and the desired slice.

* * * * *